United States Patent [19]
Ross

[11] 3,982,540
[45] Sept. 28, 1976

[54] GASTROINTESTINAL ASPIRATOR PUMP SYSTEM AND METHOD

[76] Inventor: John R. Ross, 370 Clyde St., Brookline, Mass. 02167

[22] Filed: Mar. 20, 1975

[21] Appl. No.: 560,161

Related U.S. Application Data

[63] Continuation-in-part of Ser. No. 333,871, Feb. 20, 1973, Pat. No. 3,885,567.

[52] U.S. Cl. ............................ 128/278; 128/350 R; 128/240
[51] Int. Cl.² .......................................... A61M 1/00
[58] Field of Search ........................... 128/276–278, 128/348–350, 240

[56] References Cited
UNITED STATES PATENTS

| | | | |
|---|---|---|---|
| 2,930,378 | 3/1960 | Buyers | 128/350 R |
| 3,066,672 | 12/1962 | Crosby, Jr. et al. | 128/276 |
| 3,142,298 | 7/1964 | Koski et al. | 128/276 |
| 3,429,313 | 2/1969 | Romanelli | 128/276 |
| 3,885,567 | 5/1975 | Ross | 128/278 |

*Primary Examiner*—Robert W. Michell
*Assistant Examiner*—Henry S. Layton

[57] ABSTRACT

The system includes pumps for supplying negative and positive air pressure (with respect to atmospheric air) air to the negative and positive lumens, respectively, of a multilumen tube. The lumens are separated from each other by a partition wall within the tube. The negative air pressure lumen has a plurality of apertures distributed along the outer wall of the end portion of the tube and the positive air pressure lumen has an aperture in the partition wall adjacent each of the aforesaid apertures. The negative air pressure is steadily applied, while the positive air pressure is supplied in periodic pulses. The rate at which air passes into the positive air pressure lumen is visually indicated by bubbling the air through a transparent walled vessel and the rate at which air passes out through the negative air pressure lumen is indicated by bubbling the air through another transparent walled vessel. The positive air pressure is limited by an air relief valve to a safe value. An air inlet is provided to admit air into the positive air pressure lumen whenever its pressure drops below atmospheric air pressure. The dimensions of the tube, and the various other values of pressures, times, velocity of flow are given which permit the system to be operated with a novel method for evacuating an enclosed viscus and for releasing blockages in the tube.

14 Claims, 5 Drawing Figures 3,982,540

GASTROINTESTINAL ASPIRATOR PUMP SYSTEM AND METHOD

BACKGROUND OF THE INVENTION

This application is a continuation-in-part of my copending application Ser. No. 333,871, filed Feb. 20, 1973 U.S. Pat. No. 3,885,567, issued May 27, 1975.

I have described a gastrointestinal aspirator pump system in which, by the use of a multilumen tube supplied with both positive and negative air pressure relative to atmospheric air pressure, the problem of debris or tissue blocking the passage leading into the pumping system from the gastrointestinal cavity being evacuated has been substantially solved. In such a system, as well as in gastrointestinal aspirator pump systems generally, it is highly desirable that means be provided to supply to the personnel, involved in the operation of the system, highly diagnostic indications of the conditions existing throughout the system. For example, means to indicate whether or not blockage of the exhaust lumen has occurred, whether the evacuation of the intestinal cavity has been completed and various other indications are highly to be desired. It is also desirable that, where a potentially adverse condition exists, automatic safety provisions be provided to maintain the conditions produced within the intestinal cavity well within limits which are comfortable and safe for the patient. These and other desirable features of such systems which the prior art has not been able to offer will be described in connection with the detailed description of the present invention.

SUMMARY OF THE INVENTION

The present invention provides simple and effective means for supplying the types of desirable indications as set forth above. It affords effective means for clearing blockage of the exhaust lumen. It also affords an arrangement in which, in response to the diagnostic information derived, the position of the lumen may be adjusted within the intestinal cavity with a minimum of patient discomfort. These, and other advantageous features of the present invention will be detailed below.

The desired indications are provided primarily by incorporating into the system of my copending application Ser. No. 333,871 U.S. Pat. No. 3,885,567, visual indications of the rate at which air is flowing through the positive air pressure lumen and the rate at which air is flowing out of the gastrointestinal tract through the negative air pressure lumen. In the specification and claims the terms "positive air pressure" and "negative air pressure" will be understood as being relative to atmospheric air pressure. In the embodiment illustrated herein, such indicators comprise transparent walled vessels containing liquid through which the respective air flows are bubbles, the bubble rate providing the desired air flow rate indication. Absolute control of the operative positive and negative air pressures is provided so that, in addition to providing means for removing blockages, these pressures are maintained within limits that will insure safety at all times in accordance with the physical and biological tolerances of the patient. A pressure relief valve may be inserted in the input to the positive pressure lumen to release any potentially harmful level of pressure. In addition an air leakage input from the atmosphere into the positive pressure lumen is provided so that, if such positive pressure tends to drop below atmospheric pressure, air will be drawn into the positive pressure lumen to provide an additional safety feature, as will become apparent from the more detailed description of the embodiment illustrated. The present invention also teaches various new process techniques afforded by its novel system details.

DESCRIPTION OF THE PREFERRED EMBODIMENTS

Figure 1:
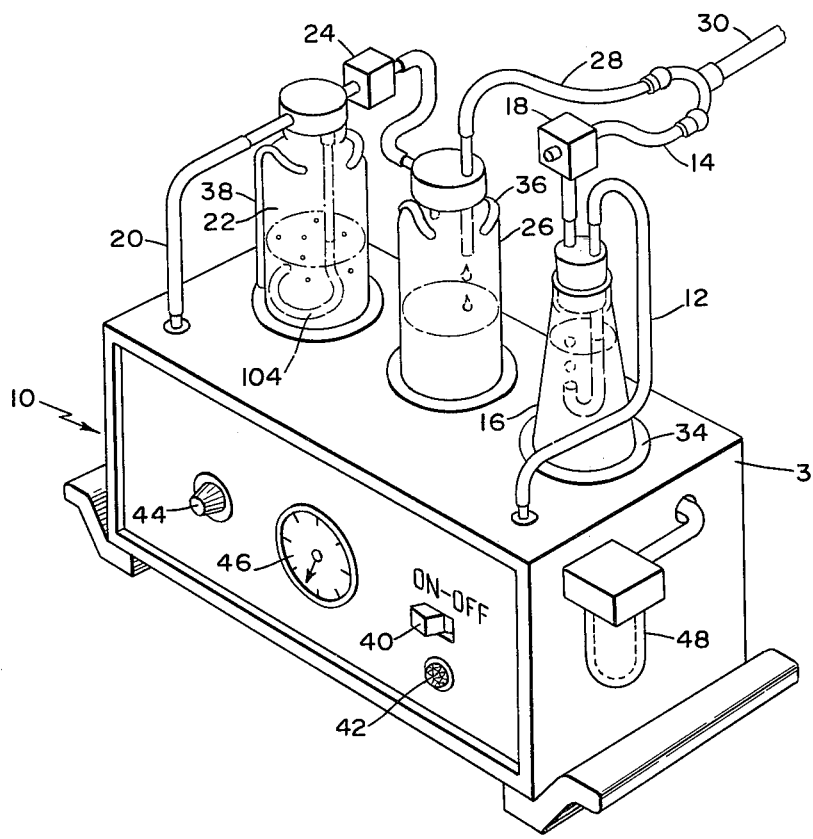
FIG. 1 is a perspective view of a gastrointestinal aspirator pump system according to the present invention.

In the modification shown in FIG. 1, the aspirator system includes a control mechanism indicated generally at 10. A positive pressure line 12, fed from the control mechanism 10, is interconnected with a positive pressure line 14 through a bubbler flask 16. A pressure relief valve 18 may be interposed in the line 14 as it is fed through flask 16. A negative pressure line 20 extends from control mechanism 10 through a bubbler jar 22, a check valve 24 and a vessel 26 for receiving the gastrointestinal fluids, to a negative pressure line 28. The positive and negative pressure lines 14 and 28 are combined into a double lumen tube 30 which is to be inserted into the gastrointestinal tract of a patient. The control mechanism 10 operates to provide a negative air pressure or suction which causes the gastrointestinal fluids to be withdrawn through line 28 and to be collected in vessel 26. Positive air pressure is supplied in line 14, in a manner and for a purpose to be described below. The control mechanism is mounted in a portable cabinet 32, the top of which is provided with suitable holders and clamps 34, 36 and 38 to support flask 16, vessel 26 and jar 22, which are thus in a position to be closely observed by the person operating the system. The front panel of cabinet 32 is provided with controls, such as an on-off switch 40, a power indicator lamp 42, a control knob 44 for regulating the magnitude of the positive air pressure, and the dial of a pressure gauge 46 for indicating the magnitude of such positive air pressure. An input air filter 48 may be mounted on a side wall of cabinet 32.

Figure 2:
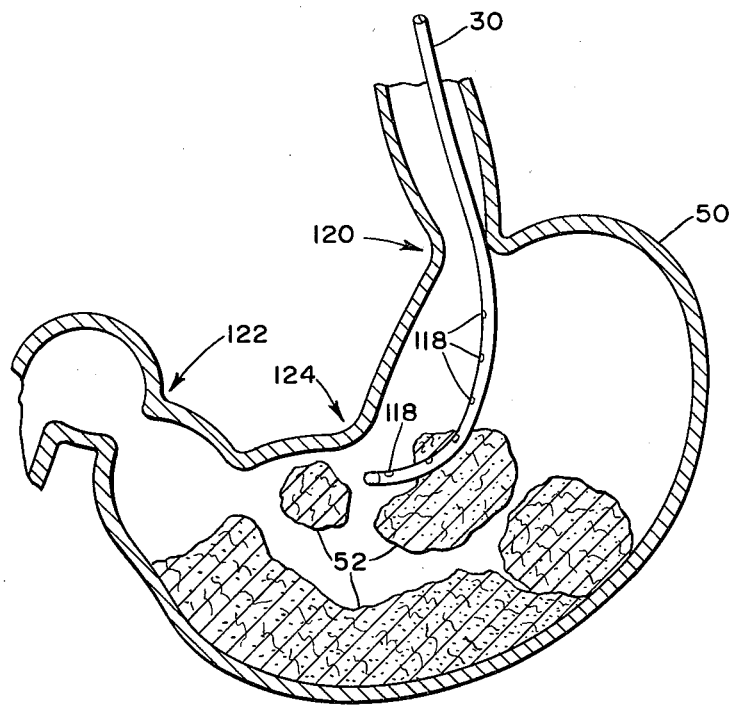
FIG. 2 is a diagram showing the disposition in a human stomach of a luman tube connected to the system of FIG. 1.

As shown in FIG. 2, tube 30, which is of sufficient length for the purpose, may be inserted into a gastrointestinal cavity such as a human stomach 50 or small intestine containing gastrointestinal fluids 52 which are to be evacuated.

Figure 3:
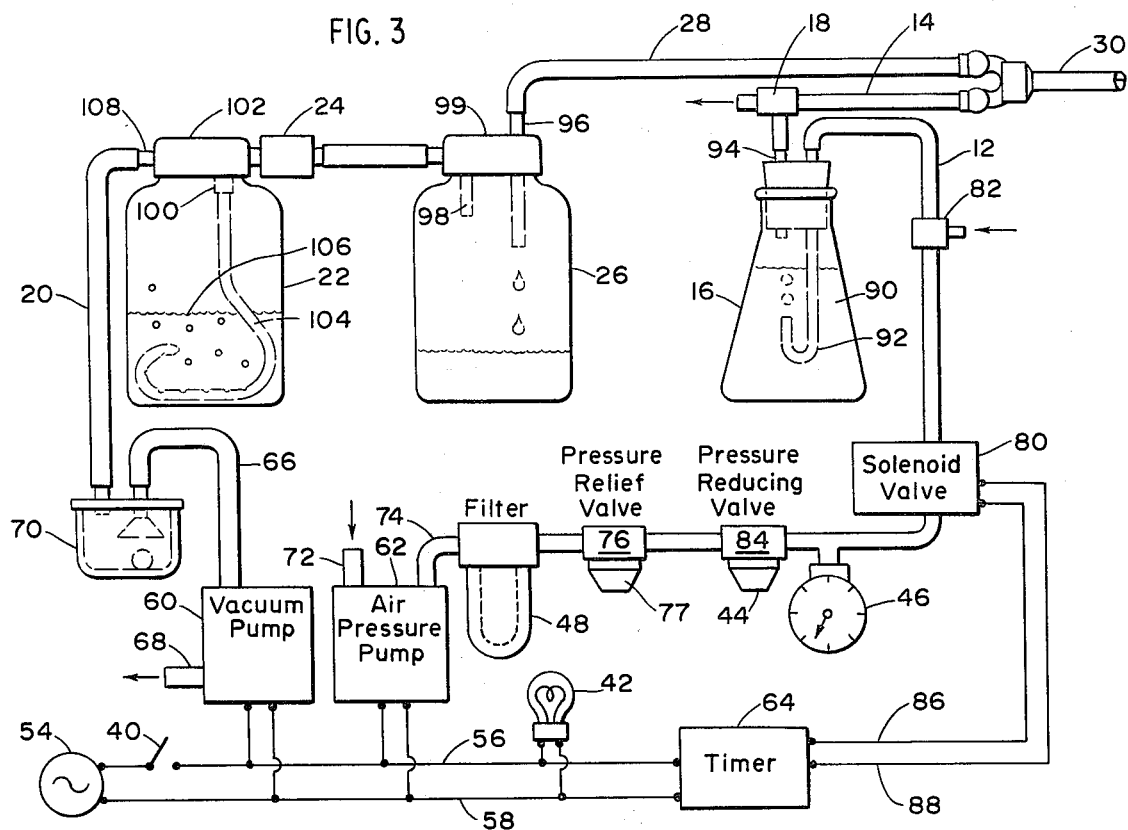
FIG. 3 is a schematic diagram of the system of FIG. 1.

The details of the system may be more clearly understood with reference to FIG. 3. Power to operate the system is provided from an electrical power source 54 such as a 120 volt, 60 cycle source. When the switch 40 is closed, power is supplied to power lines 56 and 58, which supply power to a vacuum pump 60 and an air pressure pump 62. At the same time power is supplied to an automatic timer switch 64. Indicator lamp 42 is connected across lines 56 and 58 to show when they are energized.

Vacuum pump 60 draws air in through an intake tube 66 and exhausts through an exhaust tube 68. Tube 66 is connected to negative pressure line 20 through a suction trap 70, which protects vacuum pump 60 by preventing any liquid which passes through line 20 from reaching pump 60. Suction trap 70 may also be mounted on a side wall of cabinet 32 where it may be seen readily by the operator.

Air pressure pump 62 draws air in through intake 72 and forces air out through output supply tube 74. Such air output passes successively through air filter 48, a pressure relief valve 76, a pressure reducing valve 84 and a solenoid valve 80, to the positive pressure line 12. Interposed in line 12 is an air leakage device 82 through which a small quantity of air may be drawn into line 12 from the atmosphere whenever the pressure in line 12 drops below atmospheric pressure. Pressure relief valve 76 is provided with a control knob 77 whereby the pressure relief valve 76 is set to limit its output pressure to a value, for example 2 p.s.i., which is well within the safe limits of air pressure which may be injected into the gastrointestinal cavity to be evacuated. If desired an added safety feature may be supplied by adding the pressure relief valve 18 at the input to line 14. Valve 18 is a back-up for valve 76 and operates to limit the pressure fed to line 14 should the pressure valve 76 or valve 84 be set too high or if for any other reason the pressure fed to line 14 exceeds a predetermined safe value. While the upper limit of pressure delivered to line 12 is set by relief valve 76, the actual pressure supplied to line 12 may be varied below such upper limit by a pressure reducing valve 84 under manual control of the control knob 44 mounted on the front panel of cabinet 32 as referred to above. This pressure may be read on the dial of pressure gauge 46.

The opening and closing of solenoid valve 80 is controlled by the automatic timer switch 64 which, when closed energizes lines 86 and 88 leading to the solenoid valve. Energization of these lines opens solenoid valve 80 to supply air to line 12 at the positive pressure value set by valve 84. Timer switch 64 is set to close for a predetermined period of time at longer periodic intervals. For example switch 64 may be set to close for 1/10 second at intervals of 2 seconds. As will be explained below it is significant that the time interval, during which solenoid valve delivers a pulse of positive air pressure to line 12, be relatively short as compared with the interval between such pulses.

The bubbler 16 into which line 12 leads, may be comprised of a stoppered transparent flask, nearly filled with water 90. Line 12 is connected to a U-shaped tube 92 sealed through the stopper of flask 16. The lower end of tube 92 is immersed below the level of the water 90 so that air passing from line 12 must bubble through the water 90 in order to pass out from flask 16 through a short tube 94, also sealed through the stopper of flask 16. Tube 94 connects to line 14 through valve 18.

Fluids which are evacuated from the patient's gastrointestinal cavity, in a manner as will be detailed below, flow from the double lumen tube 30 into the line 28 which is connected to a tube 96 sealed through the cap 99 of the specimen jar 26. The liquid components of these fluids, together with any solid particles, drop to the bottom of the jar 26 where they are collected so that they may later be subjected to the desired analysis. The gaseous components of the fluids are drawn off through a tube 98 sealed through cap 99, through check valve 24 and through a tube 100 sealed through the cap 102 of bubbler jar 22, into a flexible tube 104 whose lower end is perforated and lies well below the surface of the water 106 with which the jar 22 is partially filled. The gases are thus caused to bubble through the water 106 and pass out of jar 22 through a tube 108 also sealed through cap 102. Tube 108 feeds into line 20 which, as described above, is connected through suction trap 70 and intake tube 66 to vacuum pump 60. The negative air pressure generated by the vacuum pump 60 is exerted, through the path described above, into the double lumen tube 30 to drain the fluids from the gastrointestinal cavity through tube 30. Check valve 24 is provided to prevent liquids from jar 22 from backing up into jar 26 where they may dilute the desired sample collected in jar 26.

Figure 4:
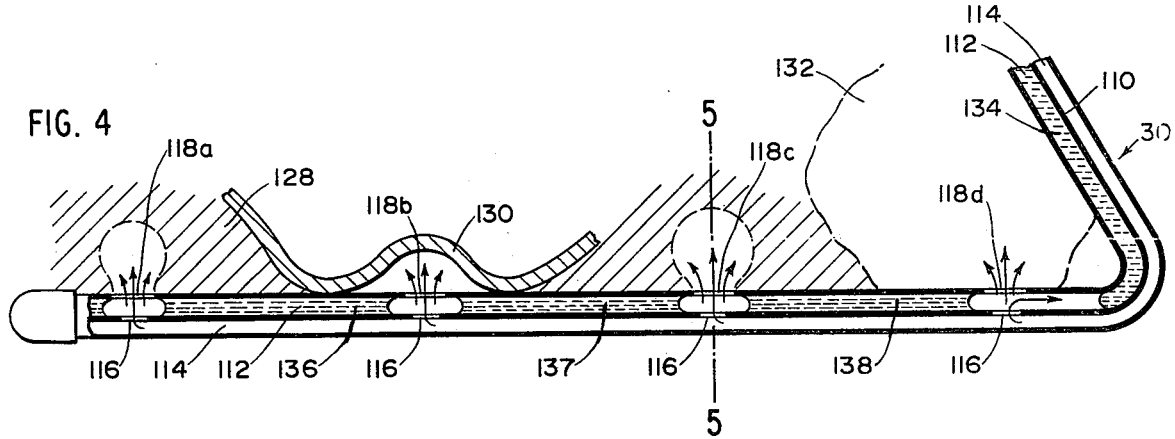
FIG. 4 is a longitudinal cross section on an enlarged scale of the distal end section of the lumen tube of FIG. 2.
Figure 5:
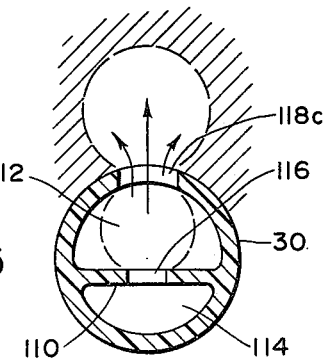
FIG. 5 is an enlarged transverse cross-section along line 5—5 of FIG. 4.

The nature of the double lumen tube 30 may be more clearly seen from the showing in FIGS. 4 and 5. It may be made of rubber, PVC, polyethylene, or other similar flexible materials. An internal wall 110 in the tube 30 forms a barrier between two lumens 112 and 114 which comprise a negative pressure and a positive pressure lumen respectively. Openings 116 in wall 110 provide passages from positive pressure lumen 114 for supplying air under positive pressure through the adjacent portions of negative pressure lumen 112 and out though openings 118 to the gastrointestinal tract. Each opening 118 is located in the outer wall of lumen 112 in line with an adjacent opening 116 from lumen 114 and is preferably of a somewhat larger diameter than that of its adjacent opening 116. The negative pressure in lumen 112 exerts an aspirator action through openings 118 on the fluids in the gastrointestinal tract to draw such fluids through such openings into lumen 112 where they are drawn off through lumen 112 into the negative pressure line 28 of the system as described for FIGS. 1 and 3.

As described in my copending application Ser. No. 333,871 U.S. Pat. No. 388,567, the emission of air under positive pressure adjacent the negative lumen openings 118 prevents blockage of such openings either by intestinal membranes or by debris, thus greatly facilitating the evacuation process. The present invention enables such a system to operate more effectively and safely and also presents novel process aspects which further expand the utility of the system.

The embodiment described above is primarily intended to operate in an enclosed viscus, such as a human stomach or small intestine as shown in FIG. 2. In this case the enclosed viscus comprises the cavity between the esophago gastric sphincter 120 and the pyloric sphincter 122. The lumen tube 30 is inserted into the cavity with its distal end located at a predetermined desired location, such as at the level of the angulus 124. A plurality of openings 118 are distributed at spaced intervals along tube 30 within the confines of the closed viscus. A typical spacing may be approximately 2 cm distributed along about 20 centimeter from the distal end of tube 30.

As is well known a typical viscus, such as the human stomach, is not a rigid hollow body but it quite flexible. It will collapse to the extent determined by the magnitude of its liquid, gaseous and solid content. Thus, as indicated diagrammatically in FIG. 2, the liquid content 52 of the stomach 50 does not necessarily lie in a pool along the bottom of the stomach, but may exist in various pockets within the partially collapsed stomach. In actual operation with the present invention, it is not necessary to locate tube 30 with any or all of its openings 118 immersed in the liquid to be evacuated. For example, with the arrangement shown in FIG. 2, when the switch 40 is closed, without any appreciable delay, pumping of the liquids in the stomach starts flowing into the specimen jar 26 even where initially none of the openings 118 was immersed in a liquid filled pocket. This phenomenum is due, at least in part, to the fact that the aspiration action of the negative air pressure in lumen 112 exerted through the openings 118 will start to evacuate whatever material is adjacent to the openings, be it gas or liquid. This lowers the content and the pressure within the stomach which proceeds to collapse still more and moves the liquid within it so that inevitably some of it will flow into a position where it covers one or more of the openings 118 and where the viscus itself covers one or more of such openings. Therefore a set of dynamic pressure conditions is created, including the pressure conditions within the positive pressure lumen 114, which forces the liquid to flow into whatever opening 118 it adjoins. A typical situation which is thus created is illustrated diagrammatically in FIG. 4 in which liquid 128 is situated adjacent openings 118a and 118c, viscus tissue 130 covers opening 118b and a pocket of gas 132 covers opening 118d. FIG. 4 represents conditions during the 1/10 sec. period of the increased positive pressure pulse. Such pressure is high enough to clear each opening 118 of any liquid, debris or tissue which may be lodged in such opening. Therefore an air bubble will be created in the liquid adjacent openings 118a and 118c, and the viscus tissue 130 will be lifted away from opening 118b and some air will escape from opening 118d into gas pocket 132. The capacity of the positive air pressure supply to lumen 114 is sufficient to maintain the predetermined pressure (e.g. 0.5psi) throughout the 1/10 second period and the small amount of air which flows out of the lumen 114 during this time is not enough to produce any substantial reduction of such positive pressure pulse. The systems may be operated in several ranges of positive and negative air pressure. However, in a typical case, the optimim positive pressure was determined to be substantially 0.5 psi and the optimim negative pressure was determined to be substantially 2.5 psi. Because of conditions existing just prior to the beginning of the 1/10 sec. period, a segment of liquid 134 will have entered lumen 112 above opening 118d and will be flowing under the influence of the negative pressure in such lumen toward its exhaust end. Air from opening 116 adjacent opening 118d can pass freely into lumen 112 behind liquid segment 134 and thus assist such segment to flow freely along lumen 112. Any pressure exerted by the air from lumen 114 will be in a direction to assist the negative pressure in lumen 112 to move the liquid segment in the desired direction. At the same time, however, the positive air pressure, which forces air through openings 118a, 118b and 118c, will create small pockets of air at the increased pressure in lumen 112 and thus temporarily stop the motion of the liquid segments 136, 137, 138 trapped between openings 118a, 118b and 118c.

As will be pointed out below, the velocity of flow of the liquid in lumen 112 above opening 118d is sufficient to completely evacuate the stomach within a period substantially less than in prior art devices. A typical linear rate of such liquid flow in the present device is about 20 cms per second. Therefore during the 1/10 second increased positive pressure pulse the segment 134 will have travelled about 2 cm, roughly about the distance between adjacent openings 118. During the 2 sec. interval between such pulses, liquid segment 134 will have travelled about 40 cms. It is important that tube 30 be designed to be greater than such length, typically about 200 cms. or roughly five times the length of travel of a liquid segment in lumen 112 between positive pressure pulses. These rates can be varied by varying the negative and positive pressure.

At the end of each 1/10 second positive pressure pulse, the pressure inside lumen 114 adjacent each opening 118 rapidly drops to a value at which the bubbles adjacent openings 118a and 118c collapse and allow liquid to enter such openings while viscus tissue 118b collapse over opening 118b, forcing the small bubble beneath it back into lumen 112. The pressure in pocket 132 will also be sufficient to cause gas to flow into lumen 112 through opening 118d. The net result of these changes is that the liquid segments 136, 137 and 138 are no longer trapped but appear to be impelled, under the combined dynamic pressure conditions produced, to move along lumen 112 past the most proximal opening 118d. This flow permits the negative pressure in lumen 112 to draw additional fluid into whatever openings 118 are immersed in a pocket of fluid.

During the following two second interval, another segment 134 is created and flows along lumen 112 as described above. The result is that in lumen 112 a series of liquid segments 134 will be flowing, each separated by a short bubble of air drawn from the most proximal opening 118 during the 1/10 second interval. Each such segment will also have entrained at its leading end a series of smaller bubbles representing those produced by the pulse of air injected adjacent each of the openings 118a, 118b and 118c. Of course the liquid may also contain other occlusions of gas which has become mixed with the gastrointestinal liquids or which otherwise enter one or more openings 118 from a pocket of gas in the intestinal cavity. As for the pocket of gas 132, during the two second interval in which the flow of liquid progresses, gas from the pocket will also be drawn into the lumen 112 and be exhausted along with the liquid. However this condition will not persist for any substantial length of time since the gas pressure in pocket 132 will drop very rapidly until either viscus tissue collapses about the opening 118d, or a pocket of liquid moves into position over such opening.

The above process continues until there are no longer any liquid segments in the lumen 112 below the most proximal opening 118d. At such time, the last liquid segment 134 continues to flow along lumen 112 followed by a continuous column of air drawn from lumen 114. As soon as such segment has passed completely out of lumen 112 all of the fluid in the intestinal cavity will have been evacuated, viscus tissue will have blocked all of the openings 118, and further evacuation of its cavity stops. At the same time it will be seen that an uninterrupted column of air fills both lumes 112 and 114. Under these conditions, negative pressure produced by vacuum pump 60 is propagated throughout the column and drops the pressure within lumen 114 sufficiently below atmospheric pressure to cause atmospheric air to flow in through the air leakage device 82. This action will produce one of the desired diagnostic indications, as will be explained below.

The above detailed explanation of the phenomena, which cause the present system to continue the evacuation of the closed intestinal cavity until it has been completely evacuated through the multiple openings 118, necessarily constitutes a simplified explanation of the complexities of the dynamic pressure and flow conditions in the system. However the use of the proper relationship between the pressures, the timing of the positive pressure pulse, the flow rate of evacuation and the dimensions of the lumen system, all as explained above, comprise a novel process made possible by this equipment.

In addition it is noted that the action of the foregoing multi-opening arrangement to completely evacuate an enclosed, and collapsible member or viscus, relies on certain physical aspects of tubes and orifices which, it is believed, have not hitherto been employed either in the specific context or broadly. For example, when the action is observed in a transparent plastic bag, one can see bubbles from a pulse of positive air emitting from the upper-most openings 118 during the period when those holes are still surrounded by liquid. But, as the liquid level drops below those openings, and the walls of the bag come up against those openings, only a small amount of air appears thereafter at those holes, and the pulse then appears to travel further down the tube where it is again effective to produce bubbles. This continues to react down the tube to the last opening, and there does not seem to be any marked tendency of the air pulse to be pulled into and lost in the first openings 116 it reaches. This is particularly noted while liquid is still in and travelling up the negative lumen, and as long as any liquid remains even at the distal end of the tube the combined effect of the pulses and suction is to draw it into the negative lumen. It is believed that this action is due to the fact that the pressure gradient in the positive air pressure pulse rises sharply (0.5 psi, 1/10 sec.), and creates a rapidly travelling pressure wave which is capable of travelling directly down the tube rather than to digress into the proximal openings 116. This action of not digressing into the proximal openings is also believed to be due in part to the mass of the collapsed walls which lie adjacent to the openings 118 once the liquid in their vicinity has entered the tube.

Accordingly it is intended herein to claim the foregoing arrangement broadly and without limitation as to the nature of the gas employed.

During the operation of the system, the appearance of bubbles percolating through the water in bubble flask 16 monitors the delivery of air to the positive pressure lumen during each of the 1/10 sec. periods. Thus the appearance of such bubbles at approximately two second intervals will inform the operator that such delivery is occurring as desired. At the same time the drawing of air out of the intestinal cavity is monitored by the appearance of gas bubbles rising in the bubble jar 22. There will be an approximate correlation between the bubble rates, the flask 16 and the jar 22 indicating to the operator that the flow of air delivered by lumen 114 is not accumulating in the gastrointestinal tract which, if not balanced by the outflow indicated by the bubbles in jar 22, could conceivably result in an undesired progressive distention of the gastrointestinal tract. Also the appearance of liquid dripping into the specimen jar 26 will indicate that evacuation of the tract is occurring. Should this visually displayed normal pattern change, the operator may immediately stop the pumping until proper assesment and correction of the problem has been accomplished.

However, in many cases, the system provides the proper assessment without stopping the operation. For example, if bubbles continue to appear in flask 16 but stop in jar 22, the operator knows that the positive air pressure pulses are keeping the openings into the gastrointestinal cavity open, but that blockage has occurred in the negative pressure lumen 112 somewhere above the most proximal opening 118. The type of debris which can cause such blockage is relatively soft and elastic and may be dislodged by alternately compressing and expanding it. This may be done by the operator manipulating control knob 44 to periodically increase and decrease the pressure exerted behind the blockage. Also the pump 60 may be supplied with a control to increase and decrease the negative pressure which it exerts on the blockage. By manipulating these controls in opposite directions, the blockage is usually quite readily dislodged and the evacuation system continued without interruption.

When the gastrointestinal cavity has been completely evacuated, all of the openings 118 will be blocked by the collapsed viscus, without however such viscus being drawn into any of the openings. At that time, the negative lumen 112 will be completely void of liquid and the unimpeded flow of air between the positive and negative lumens, as previously described will occur. The resultant inflow of air through air leakage device 82 will produce a more rapid and steady flow of bubbles in both flask 16 and jar 22. This gives the operator an immediate indication that evacuation is complete, and that the pumping may be stopped.

It has been found that the present system has greatly improved the efficiency of the technique of evacuating a closed viscus. For example, whereas prior art devices have required about 12 minutes to evacuate a viscus of 30 milliliters of liquid plus its air content, the present system accomplished the evacuation in 25 seconds. In prior art systems, it has been difficult, if not impossible to maintain precise control in timed evacuations, whereas in the present system, with given pressure and time settings, the time to evacuate a given volume of fluid is directly proportional to the volume of fluid. This feature is especially important in studies where aliquot controls are concerned.

Other observations with the use of the present invention have demonstrated additional advantages. For example, where prior art endoscopes encountered mucous lakes within the stomach which were not readily removed, distortion of the field of investigation resulted. However, the present multilumen device rapidly withdrew all fluid and mucous debris, leaving a dry stomach. Other advantages have been demonstrated such as increased patient comfort, the ability of the patient to be placed in conventional upright sitting position and the ability of being able to move the location of the tube easily and with minimal patient discomfort. Where additional substances, such as chemicals for analytical purposes, are introduced into a gastrointestinal cavity, the present invention may be used to drain such substances from the cavity in order to perform the desired analysis. This invention also has decompression application to gastrointestinal distention of medical or surgical origin.

Various modifications of the embodiment described above may be made without departing from the spirit of the present invention. For example, instead of the device being a simple air leakage device it could be in the form of a flap or needle valve which opens to permit air to enter the positive pressure line 12 whenever the pressure in the line falls below ambient room pressure. Instead of providing a plurality of apertures distributed along the tube, many of the advantages of the present invention may be obtained with even a simple aperture in the outer wall of the negative pressure lumen. Although the operation of the above embodiment has been described in evacuating an enclosed viscus, the present invention may also be adapted for use in the drainage of open cavities exposed to the atmosphere as in the cases of abdominal and thoracic wound cavities and in dental and pharyngeal procedures. In such cases the single external aperture type of double lumen tube is preferred. However a greater number of such apertures may also be used, except in that case it is preferred that all openings be immersed in the liquid which is to be drained. Where desired, gases other than air may be used to produce the pressure variations as described above. Therefore the term "gas" will be used in the claims in the generic sense to include such other gases as well as air. In addition the gas can be employed to entrain additional medication or analytical fluids. These and other modifications, which will suggest themselves to those skilled in the art are intended to be within the scope of the present invention as defined in the appended claims.

I claim:

1. An aspirator pump and tube system for draining liquid from a human cavity comprising:
   a. a mulitlumen tube, a portion of which is adapted to be inserted into such cavity, having a positive gas pressure lumen and a negative gas pressure lumen, said lumens being separated from each other by a partition wall within said tube;
   b. means for supplying negative pressure gas to said negative gas pressure lumen;
   c. means for supplying a plurality of positive gas pressure pulses to said positive gas pressure lumen, each of said pulses being of a first predetermined time duration and being spaced from each other by a second predetermined time duration;
   d. said negative gas pressure lumen having a first aperture in an outside wall of said tube in the portion adapted to be inserted into such cavity, and said positive gas pressure lumen having a second aperture in said portion wall adjacent said first aperture;
   e. indicator means responsive to the flow of gas into said positive gas pressure lumen for indicating the rate of said flow, and
   f. indicator means responsive to the flow of gas out of said negative gas pressure lumen for indicating the rate of said latter flow.

2. A system as in claim 1 in which each of said indicator means comprises means for providing a visual indication of said gas flow rates.

3. A system as in claim 1 in which each of said indicator means comprises a transparent walled vessel containing liquid and means for bubbling the flow of gas to be measured through said liquid.

4. A system as in claim 1 in which said positive gas pressure lumen has an inlet end into which said positive gas pressure pulses are supplied and which also comprises air inlet means adapted to be exposed to atmospheric air, said air inlet means being adapted to admit atmospheric air into said positive gas pressure lumen whenever the pressure in said positive gas pressure lumen drops below atmospheric air pressure.

5. A system as in claim 1 in which said positive pressure lumen has an inlet end into which said positive gas pressure pulses are supplied and which also comprises pressure limiting means interposed between said means for supplying positive gas pressure pulses and said inlet end, said pressure limiting means being adapted to limit the pressure of said positive gas pressure pulses to below a preselected maximum.

6. A system as in claim 1 in which said means for supplying said negative gas pressure gas and said positive gas pressure gas are adapted to produce a preselected maximum gas pressure difference between them, said system also comprising operator controllable means for varying said difference.

7. A system as in claim 1 in which said portion of said tube adapted to be inserted into a human cavity is formed with a plurality of said first and second apertures distributed along said portion.

8. A system as in claim 1 in which the total length of said tube is more than twice the distance along which said apertures are distributed.

9. The method of draining fluid from an enclosed viscus by means of an elongated multilumen tube having a positive gas pressure lumen and a negative gas pressure lumen separated from each other by a partition wall within said tube, an end portion of said tube having a plurality of apertures in an outward wall of said negative gas pressure lumen distributed along said end portion and said positive gas pressure lumen having an aperture in said portion wall adjacent each of said first named apertures, which method consists in:
   a. inserting said end portion into said enclosed viscus;
   b. supplying negative gas pressure to said negative gas pressure lumen and supplying pulses of positive pressure gas to said positive gas pressure lumen;
   c. maintaining the values of said negative gas pressure and said positive gas pressure to propel any liquid which enters any aperture in said negative gas pressure lumen at a predetermined velocity; and
   d. maintaining the time interval between successive positive gas pulses at a value at which said liquid travels at said predetermined velocity along said negative gas pressure lumen a distance which is substantially less than the total length of said negative gas pressure lumen.

10. The method of dislodging blockage from openings in a multilumen tube during the draining of a human cavity, in which said multilumen tube has a positive gas pressure lumen and a negative gas pressure lumen separated from each other by a partition wall within said tube and in which an outside wall of said negative pressure lumen is provided with an aperture in an outside wall of said tube and said positive pressure lumen has an aperture in said partition wall adjacent said first named partition, which method consists of:
   a. inserting the portion of said tube provided with said apertures into said cavity;
   b. supplying negative and positive gas pressures to said negative and positive gas pressure lumens respectively; and
   c. exerting a varying degree of compression and expansion on the blockage to be released by varying the maximum pressure difference between said positive and negative air pressures until said blockage is dislodged.

11. The method of claim 10 in which the gas in said positive gas pressure lumen is employed to entrain additional substances.

12. Apparatus for evacuating a cavity comprising:
 a. a multilumen tube for insertion into said cavity;
 b. means for supplying gas under positive pressure, relative to atmospheric air pressure, to one of said lumens;
 c. means for drawing gas from and thereby to create negative pressure, relative to atmospheric air pressure, in another of said lumens;
 d. a partition wall between said positive and negative pressure lumens;
 e. a series of openings spaced longitudinally of said partition wall whereby gas may enter said negative pressure lumen from said positive pressure lumen;
 f. further openings in said negative pressure lumen leading to said cavity, one of said further openings being located substantially adjacent to each opening in said partition wall;
 g. indicator means responsive to the flow of gas into said positive gas pressure lumen for indicating the rate of said flow;
 h. indicator means responsive to the flow of gas and of said negative pressure lumen for indicating the rate of said latter flow; and
 whereby a plurality of openings spaced longitudinally of said tube are effective in evacuating said cavity.

13. A system as in claim 12 wherein said indicator means responsive to the flow of gas into positive gas pressure lumen evidences a continuous stream of gas upon at least substantially complete draining of fluid from said human cavity.

14. A system as in claim 12 wherein said indicator means responsive to the flow of gas out of said negative gas pressure lumen evidences a cessation of said flow of gas upon blockage in said negative gas pressure lumen above the most proximal first aperture.

* * * * *

UNITED STATES PATENT OFFICE
CERTIFICATE OF CORRECTION

Patent No. 3,982,540   Dated September 28, 1976

Inventor(s) John R. Ross

It is certified that error appears in the above-identified patent and that said Letters Patent are hereby corrected as shown below:

Column 1, line 56 "bubbles" should be
-- bubbled --

Column 6, line 59 "lumes" should be
-- lumens --

Column 12, line 11 "into positive gas" should be
-- into said positive gas --

Signed and Sealed this

Fourteenth Day of December 1976

[SEAL]

Attest:

RUTH C. MASON
*Attesting Officer*

C. MARSHALL DANN
*Commissioner of Patents and Trademarks*